(12) United States Patent
Yabe et al.

(10) Patent No.: US 9,417,200 B2
(45) Date of Patent: Aug. 16, 2016

(54) MOISTURE CONCENTRATION DETECTING DEVICE

(75) Inventors: Tatsuya Yabe, Tokyo (JP); Yoshiyuki Tamura, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 295 days.

(21) Appl. No.: 14/355,861

(22) PCT Filed: Apr. 2, 2012

(86) PCT No.: PCT/JP2012/058974
§ 371 (c)(1),
(2), (4) Date: May 2, 2014

(87) PCT Pub. No.: WO2013/073213
PCT Pub. Date: May 23, 2013

(65) Prior Publication Data
US 2015/0075255 A1    Mar. 19, 2015

(30) Foreign Application Priority Data

Nov. 18, 2011  (JP) ................................ 2011-252728

(51) Int. Cl.
*G01N 27/04* (2006.01)
*G01N 33/00* (2006.01)

(52) U.S. Cl.
CPC .......... *G01N 27/048* (2013.01); *G01N 33/0036* (2013.01)

(58) Field of Classification Search
CPC ................................................... G01N 27/048
See application file for complete search history.

(56) References Cited

U.S. PATENT DOCUMENTS 3,983,527 A * 9/1976 Ohsato .................. G01N 27/121
200/61.04

7,189,572 B2 * 3/2007 Imamura .............. G01N 27/048
422/68.1

(Continued)

FOREIGN PATENT DOCUMENTS

JP    54-33793       3/1979
JP    58-66044  A    4/1983

(Continued)

OTHER PUBLICATIONS

International Search Report (PCT/ISA/210) mailed on Jun. 26, 2012, by the Japanese Patent Office as the International Searching Authority for International Application No. PCT/JP2012/058974.

(Continued)

*Primary Examiner* — Hezron E Williams
*Assistant Examiner* — Mark A Shabman
(74) *Attorney, Agent, or Firm* — Buchanan Ingersoll & Rooney PC

(57) ABSTRACT

A moisture concentration detecting device including a gas chamber; a pair of porous electrodes facing each other in the gas chamber; a solid electrolyte membrane sandwiched between the electrodes; a case which covers the electrodes and the solid electrolyte membrane and on a surface of which a pleated portion is provided; an impedance measuring circuit measuring an AC impedance between the electrodes by applying an AC voltage to the electrodes; a storage device storing therein conversion information for converting an AC impedance between the electrodes into a moisture concentration in the insulating gas; and a computing unit obtaining a moisture concentration in the insulating gas from a measured value of the AC impedance by referring to the conversion information stored in the storage device with respect to the measured value of the AC impedance input from the impedance measuring circuit.

4 Claims, 4 Drawing Sheets

(56) References Cited

U.S. PATENT DOCUMENTS

| | | | | |
|---|---|---|---|---|
| 9,201,033 | B2* | 12/2015 | Nishida | G01N 27/02 |
| 9,201,034 | B2* | 12/2015 | Martin | G01R 35/005 |
| 2005/0081625 | A1* | 4/2005 | Chen | B82Y 30/00 |
| | | | | 73/335.02 |
| 2005/0233463 | A1* | 10/2005 | Dominelli | G01N 33/0042 |
| | | | | 436/119 |
| 2009/0182244 | A1* | 7/2009 | Hoenes | A61B 5/1411 |
| | | | | 600/583 |
| 2013/0319111 | A1* | 12/2013 | Yabe | G01N 27/121 |
| | | | | 73/335.03 |

FOREIGN PATENT DOCUMENTS

| | | |
|---|---|---|
| JP | 58-106446 A | 6/1983 |
| JP | 59-17847 U | 2/1984 |
| JP | 63-43330 U | 3/1988 |
| JP | 5-2034 A | 1/1993 |
| JP | 5-60716 A | 3/1993 |
| JP | 2001-186613 A | 7/2001 |
| JP | 2001-258113 A | 9/2001 |
| JP | 2002-250710 A | 9/2002 |
| JP | 2004-177263 A | 6/2004 |
| JP | 2005-83960 A | 3/2005 |
| JP | 2006-38591 A | 2/2006 |
| JP | 2006-90812 A | 4/2006 |
| JP | 2006-98383 A | 4/2006 |
| JP | 2006-308502 A | 11/2006 |
| JP | 2009-266743 A | 11/2009 |

OTHER PUBLICATIONS

Written Opinion (PCT/ISA/237) mailed on Jun. 26, 2012, by the Japanese Patent Office as the International Searching Authority for International Application No. PCT/JP2012/058974.

Eiichi Nagao et al., Moisture Detection of $SF_6$ Gas Instruments by Solid Electrolyte, Helsi 17 Nen National Convention Record I.E.E. Japan, 2005, pp. 244-245.

Eiichi Nagao et al., Moisture Detection of $SF_6$ Gas Instruments by Solid Electrolyte, Helsel 17 Nen Proceedings of the Annual Conference of Power & Energy Society, 2005, pp. 40-1-40-2.

Mitsuhito Kamei et al., Study of Water Detecting Sensor in Insulated Gas of GIS/GCB Eletrochemical Sensor Using Ttriethlenediaminesulfate as Electrolyte, The Transactions of the Institute of Electric Engineers of Japan, Nov. 2, 2010, vol. 130, No. 11, pp. 531-536.

* cited by examiner

MOISTURE CONCENTRATION DETECTING DEVICE

FIELD

The present invention relates to a moisture concentration detecting device that detects a moisture concentration in an insulating gas with which a gas insulating device is filled.

BACKGROUND

Gas insulating devices are filled with an insulating gas, such as an $SF_6$ gas. With conventional moisture concentration detecting devices, the moisture sensors, which detect moisture, are arranged in the gas insulating devices. The moisture sensors are configured to include porous electrodes provided to face each other and a hydrogen-ion conductive solid electrolyte membrane that is provided between the porous electrodes and is in equilibrium with the moisture concentration in an $SF_6$ gas. The moisture concentration detecting devices measure the moisture concentration in the $SF_6$ gas by applying an AC voltage across the porous electrodes and measuring the AC impedance between the electrodes, which changes in accordance with the moisture concentration in the $SF_6$ gas (see Patent Literature 1).

CITATION LIST

Patent Literature

Patent Literature 1: Japanese Patent Application Laid-open No. 2006-308502

SUMMARY

Technical Problem

In the gas insulating devices that are currently in practical use, an $SF_6$ gas is pyrolyzed, for example, by the arc generated due to the breaking operation of a breaker, whereby decomposition products thereof are generated. If the surface of the moisture sensor element or the surface of the case covering the element becomes contaminated by the decomposition products adhering thereto, the surface resistance of the whole moisture sensor decreases.

On the other hand, the AC impedance of the solid electrolyte membrane reaches a value as high as several $M\Omega$ or even higher in an atmosphere where the moisture concentration is as low as several tens of ppm or even lower; therefore, it is required to measure a microcurrent in order to detect the moisture concentration.

Therefore, if the surface resistance of the moisture sensor decreases due to the decomposition products of the $SF_6$ gas, the effect of the leakage current that flows on the surface of the moisture sensor increases. Consequently, there is a problem in that the measurement error of the AC impedance increases and thus it becomes difficult to correctly measure the moisture concentration.

The present invention has been achieved in view of the above and an object of the present invention is to provide a moisture concentration detecting device for a gas insulating device, which enables the moisture concentration to be measured with high accuracy by reducing the effect of contamination of the surface of the moisture sensor by decomposition products of an insulating gas.

Solution to Problem

In order to solve the above problems and achieve the object, a moisture concentration detecting device according to the present invention is a moisture concentration detecting device that detects a moisture concentration in an insulating gas with which a gas insulating device is filled, the device including: a gas chamber into which the insulating gas is introduced from an inside of the gas insulating device; a pair of porous electrodes that are arranged to face each other in the gas chamber; a solid electrolyte membrane fixed such that the solid electrolyte membrane is sandwiched between the electrodes; a case which covers the pair of electrodes and the solid electrolyte membrane and on a surface of which a pleated portion is provided; an impedance measuring unit that measures an AC impedance between the electrodes by applying an AC voltage to the pair of electrodes; a storage device that stores therein conversion information for converting an AC impedance between the electrodes into a moisture concentration in the insulating gas; and a moisture concentration detecting unit that obtains a moisture concentration in the insulating gas from a measured value of the AC impedance by referring to the conversion information stored in the storage device with respect to the measured value of the AC impedance input from the impedance measuring unit.

Advantageous Effects of Invention

According to the present invention, an effect is obtained where it is possible to provide a moisture concentration detecting device for a gas insulating device, which enables the moisture concentration to be measured with high accuracy by reducing the effect of contamination of the surface of the moisture sensor by decomposition products of an insulating gas.

DESCRIPTION OF EMBODIMENTS

Exemplary embodiments of a moisture concentration detecting device according to the present invention will be explained below in detail with reference to the drawings. This invention is not limited to the embodiments.

First Embodiment

Figure 1:
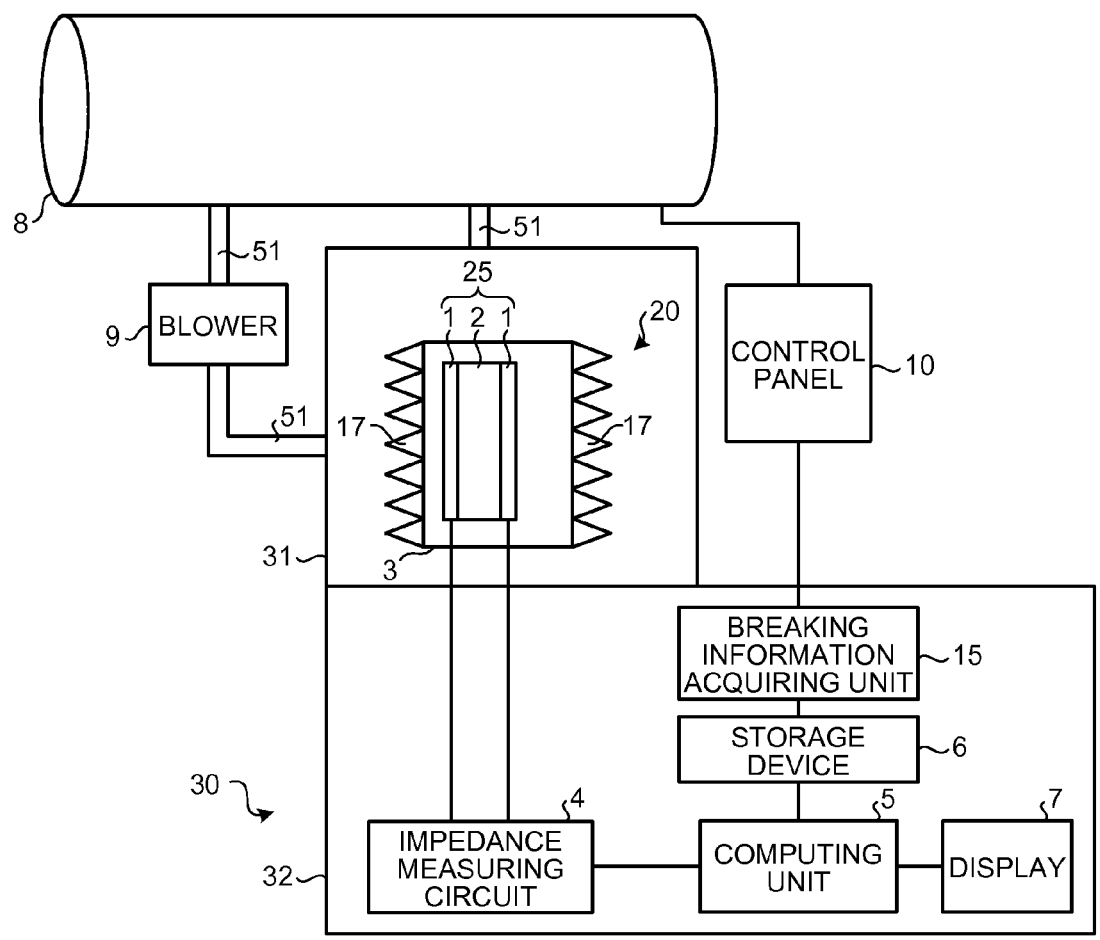
FIG. 1 is a diagram illustrating the configuration of a moisture concentration detecting device according to a first embodiment.

FIG. 1 is a diagram illustrating the configuration of a moisture concentration detecting device according to the present embodiment. FIG. 1 illustrates a gas insulating device 8 in which a metal container is filled with an insulating gas, a moisture concentration detecting device 30 that is connected to the gas insulating device 8, and a control panel 10 of the gas insulating device 8. The insulating gas is, for example, an $SF_6$ gas. Moreover, the gas insulating device 8 is, for example, a gas insulated circuit breaker including a breaking unit. The control panel 10 performs a control, such as an open/close control of the gas insulating device 8.

The moisture concentration detecting device 30 is connected to the gas insulating device 8, for example, via two pipes 51. The insulating gas in the gas insulating device 8 is introduced into the moisture concentration detecting device 30 through the pipes 51 and is used as a sampling gas for measuring the moisture concentration. Moreover, in the example in FIG. 1, one of the pipes 51 is provided with a blower 9. The blower 9 can blow the insulating gas to be introduced into the moisture concentration detecting device 30 from the inside of the gas insulating device 8. The configuration may be such that both the pipes 51 are provided with the blower 9.

The moisture concentration detecting device 30 includes a gas chamber 31 and a signal processing chamber 32. The gas chamber 31 is connected to the gas insulating device 8 via the pipes 51 and the insulating gas can be introduced from the inside of the gas insulating device 8 by opening the valve (not illustrated). In this case, a gas convection environment can be created in the gas chamber 31 by driving the blower 9. An impedance element 25, which includes a pair of porous electrodes 1 arranged to face each other and a solid electrolyte membrane 2 fixed such that it is sandwiched between the electrodes 1, is arranged in the gas chamber 31.

The electrodes 1 are formed, for example, by performing electroless plating on platinum and are microscopically porous. With the use of the electrodes 1, the moisture in the insulating gas easily permeates the solid electrolyte membrane 2. The solid electrolyte membrane 2 is, for example, made of a hydrogen-ion conductive polymer and the moisture content thereof is in equilibrium with the moisture concentration in the insulating gas. In other words, if the moisture concentration in the insulating gas increases, the moisture content increases, and, in contrast, if the moisture concentration in the insulating gas decreases, the moisture content decreases. For the solid electrolyte membrane 2, for example, Nafion (NAFION (registered trademark)) manufactured by Du Pont Corporation can be used.

The electrodes 1 and the solid electrolyte membrane 2 are covered with a case 3 (case unit) and are accommodated in the case 3. The case 3 is, for example, made of a resin and the electrodes 1 and the solid electrolyte membrane 2 are, for example, press-fitted in the case 3. An opening (not illustrated) is provided in the case 3 such that the insulating gas in the gas chamber 31 is introduced into the case 3 and can come into contact with the electrodes 1 and the solid electrolyte membrane 2. Moreover, the electrodes 1 are in contact with the case 3.

A pleated portion 17 is provided on the surface of the case 3. The pleated portion 17 is provided, for example, uniformly on the surface of the case 3 and serves to increase the surface area of the case 3 compared with a case where the surface thereof is flat. The specific shape of the pleated portion 17 is not set and it is typically satisfactory if the pleated portion 17 forms an irregular shape and increases the surface area of the case 3.

A moisture sensor 20 in the present embodiment is configured to include the solid electrolyte membrane 2, a pair of the porous electrodes 1 between which the solid electrolyte membrane 2 is sandwiched, and the case 3 that accommodates therein the electrodes 1 and the solid electrolyte membrane 2 and is provided with the pleated portion 17.

An impedance measuring circuit 4, a computing unit 5, a storage device 6, a display 7, and a breaking information acquiring unit 15 are provided in the signal processing chamber 32.

The impedance measuring circuit 4 (impedance measuring unit) is connected to the electrodes 1. The impedance measuring circuit 4 measures the AC impedance between the electrodes 1 by applying an AC voltage to the electrodes 1. The impedance measuring circuit 4 outputs the measured value of the AC impedance to the computing unit 5. The impedance measuring circuit 4 is, for example, configured to include an AC power source (not illustrated) that applies a voltage to the electrodes 1, a dividing resistor (not illustrated) that detects the AC current flowing between the electrodes 1 in a state where a voltage is applied by the AC power source, and the like. Details are described, for example, in Patent Literature 1 and are therefore omitted.

The breaking information acquiring unit 15 is connected to the control panel 10. The control panel 10 outputs a breaker operation signal to the breaking information acquiring unit 15 every time the breaker operates. The breaking information acquiring unit 15 increments the number of breaker operations every time the breaker operation signal is received and records the result thereof in the storage device 6. In other words, the breaking information acquiring unit 15 updates the cumulative number of breaker operations on the basis of the breaker operation signal from the control panel 10 and records the result thereof in the storage device 6. Due to the breaking operation of the breaker, an arc current is generated and the insulating gas is decomposed by the arc current, whereby decomposition products thereof are generated. Typically, as the cumulative number of breaker operations increases, the amount of decomposition products generated increases. This affects the contamination of the surface of the moisture sensor 20.

Figure 2:
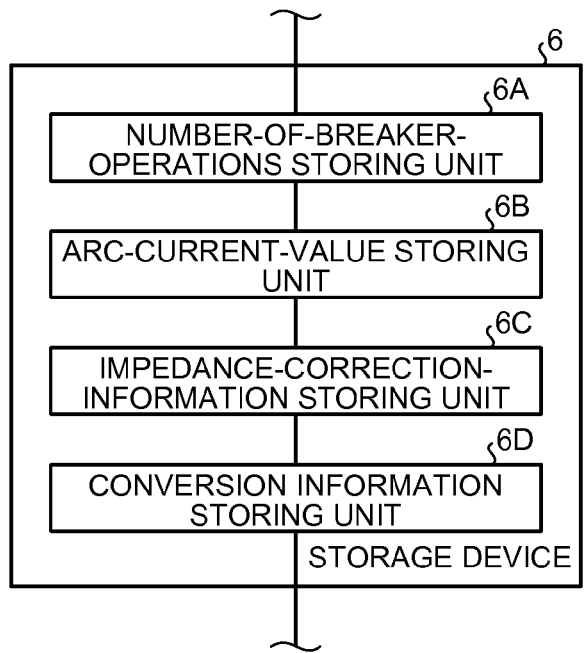
FIG. 2 is a diagram illustrating one example of the internal configuration of a storage device 6.

The storage device 6 is connected to each of the breaking information acquiring unit 15 and the computing unit 5. FIG. 2 is a diagram illustrating one example of the internal configuration of the storage device 6. As illustrated in FIG. 2, the storage device 6 includes a number-of-breaker-operations storing unit 6a, an arc-current-value storing unit 6b, an impedance-correction-information storing unit 6c, and a conversion information storing unit 6d.

The number-of-breaker-operations storing unit 6a stores therein information (cumulative-number-of-breaker-operations information) on the cumulative number of breaker operations, which is output from the breaking information acquiring unit 15.

The arc-current-value storing unit 6b stores therein information (arc-current-value information) on the current value of an arc generated when the breaker operates. Because it is difficult to actually measure the arc current value, the arc-current-value information stored in the arc-current-value storing unit 6b is set to a current value that is estimated, for example, in accordance with the rated voltage of the gas insulated circuit breaker. The arc-current-value information may be, for example, information obtained by storing the information output from the control panel 10 in the arc-current-value storing unit 6b via the breaking information acquiring unit 15 or may be information stored in the arc-current-value storing unit 6b in advance separately from the above information. Typically, as the arc current value increases, the amount of decomposition products generated increases. This affects the contamination of the surface of the moisture sensor 20.

The impedance-correction-information storing unit 6c stores therein the impedance correction information for correcting the measured value of the AC impedance output from the impedance measuring circuit 4 in accordance with the cumulative number of breaker operations and the arc current value. The impedance correction information is, for example, information on a correction curve or a correction formula that gives a correction factor that corrects the measured value of the AC impedance in accordance with the cumulative number of breaker operations and the arc current value. When AC impedance is measured by using the moisture sensor 20, if the surface of the moisture sensor 20 is contaminated by decomposition products of the insulating gas and the surface resistance of the moisture sensor 20 decreases, the measured value of the AC impedance may include an error due to the contamination. Therefore, the impedance-correction-information storing unit 6c, for example, prestores the impedance correction information generated on the basis of the actual measurement or the like so that the measured value of the AC impedance affected by the contamination of the surface of the moisture sensor 20 can be corrected.

Figure 3:
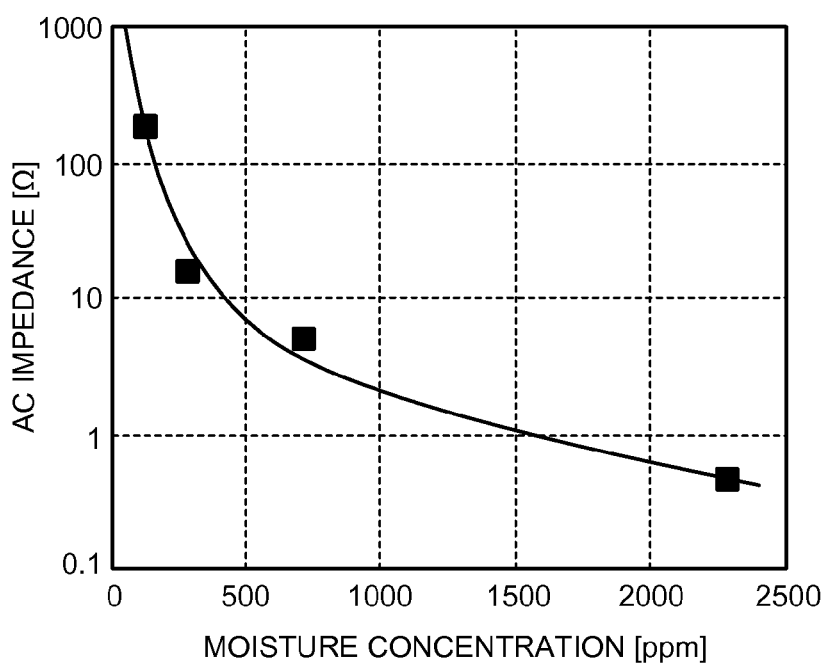
FIG. 3 is a graph illustrating one example of the relationship between the moisture concentration (ppm) in the insulating gas and the AC impedance ($\Omega$) of a solid electrolyte membrane 2.

The conversion information storing unit 6d stores therein the conversion information for obtaining the moisture concentration in the insulating gas from the AC impedance. Under conditions where the temperature of the insulating gas is constant, the moisture concentration in the insulating gas and the AC impedance of the solid electrolyte membrane 2 have a relationship, for example, as illustrated in FIG. 3 (see Patent Literature 1). FIG. 3 is a graph illustrating the relationship between the moisture concentration (ppm) in the insulating gas and the AC impedance ($\Omega$) of the solid electrolyte membrane 2 when the temperature is at a certain constant value and the graph is generated on the basis of the measurement result. In this embodiment, FIG. 3 illustrates a result in a case where the power supply frequency is 50 Hz as one example. As described above, the conversion information is data in which the AC impedance is associated with the moisture concentration and is, for example, AC impedance— moisture concentration curve data as illustrated in FIG. 3.

The computing unit 5 (moisture concentration detecting unit) calculates the moisture concentration in the insulating gas on the basis of the measured value of the AC impedance output from the impedance measuring circuit 4. Specifically, the computing unit 5 performs the following process. First, when the measured value of the AC impedance is input from the impedance measuring circuit 4, the computing unit 5 obtains information on the cumulative number of breaker operations and on the arc current value by referring to the number-of-breaker-operations storing unit 6a and the arc-current-value storing unit 6b, respectively. Next, the computing unit 5 obtains the impedance correction information corresponding to the cumulative number of breaker operations and the arc current value by referring to the impedance-correction-information storing unit 6c and corrects the measured value of the AC impedance by using the impedance correction information. Then, the computing unit 5 refers to the conversion information in the conversion information storing unit 6d and applies the conversion information to the corrected measured value of the AC impedance to convert the corrected measured value of the AC impedance into the moisture concentration, thereby obtaining the moisture concentration in the insulating gas.

The display 7 can display the output of the computing unit 5, which is, specifically, the moisture concentration in the insulating gas. The moisture concentration detecting device 30 further includes an input unit for, for example, controlling the device itself and the like; however, they are not illustrated.

Next, the operation of the present embodiment will be explained. When measurement of the moisture concentration is started, the insulating gas in the gas insulating device 8 is caused to flow into the gas chamber 31 via the pipes 51. At this point, the insulating gas can be blown in by driving the blower 9. When the insulating gas is introduced into the gas chamber 31, the amount of moisture contained in the solid electrolyte membrane 2 comes to equilibrium with the amount of moisture contained in the insulating gas in the gas insulating device 8 over time. When an AC voltage is applied across both sides of the electrodes 1 from the outside, the AC impedance in accordance with the moisture concentration in the solid electrolyte membrane 2 is measured by the impedance measuring circuit 4.

On the other hand, a breaker operation signal is output from the local control panel 10 every time the breaking unit of the gas insulating device 8 operates. The breaking information acquiring unit 15 detects this breaker operation signal and records in the storage device 6 the cumulative number of breaker operations from the time when the gas insulating device 8 is arranged.

Next, the computing unit 5 performs a correcting process on the AC impedance value measured by the impedance measuring circuit 4 on the basis of the impedance correction information stored in the storage device 6 in accordance with the cumulative number of breaker operations and the arc current value recorded in the storage device 6 and performs a process of converting the corrected AC impedance value into the moisture concentration by using the conversion information stored in the storage device 6. The computing unit 5 displays the obtained moisture concentration on the display 7.

Figure 4:
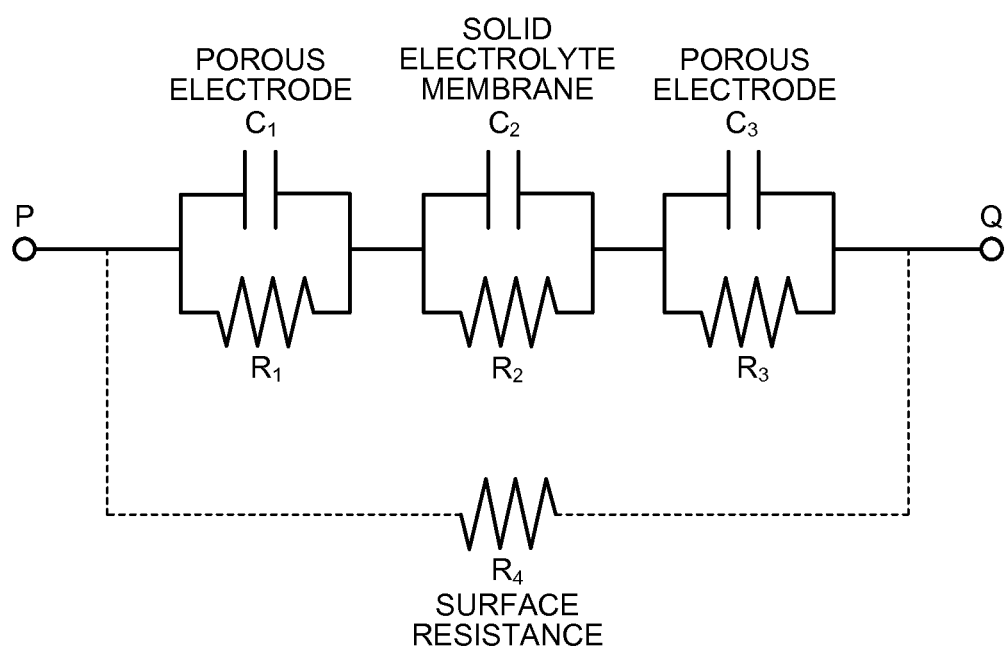
FIG. 4 is a diagram illustrating an equivalent circuit of a moisture sensor 20.

Next, an equivalent circuit of the moisture sensor 20 will be explained with reference to FIG. 4. FIG. 4 is a diagram illustrating an equivalent circuit of the moisture sensor 20. One of the porous electrodes 1 of a pair can be represented by a parallel circuit of a resistor having a resistance $R_1$ and a capacitor having a capacitance $C_1$. The other of the porous electrodes 1 of the pair can be represented by a parallel circuit of a resistor having a resistance $R_3$ and a capacitor having a capacitance $C_3$. In a similar manner, the solid electrolyte membrane 2 can be represented by a parallel circuit of a resistor having a resistance $R_2$ and a capacitor having a capacitance $C_2$.

The resistance $R_2$ and the capacitance $C_2$ of the solid electrolyte membrane 2 change depending on the moisture concentration contained in the solid electrolyte membrane 2; therefore, the impedance measuring circuit 4 can measure the combined impedance of the whole series circuit by measuring the current flowing in the series circuit that includes one of the porous electrodes 1 ($R_1$, $C_1$), the other of the porous electrodes 1 ($R_3$, $C_3$), and the solid electrolyte membrane 2 ($R_1$, $C_1$) sandwiched between them.

On the other hand, when the amount of moisture contained in the solid electrolyte membrane 2 decreases, the combined impedance thereof reaches a value as high as several M$\Omega$; therefore, it is required to measure a microcurrent in order to detect the moisture concentration. In such a case, the effect of the leakage current flowing through a surface resistance $R_4$ of the case 3 and the like increases; therefore, the measurement error of the moisture concentration increases as the surface resistance $R_4$ becomes smaller.

Moreover, when the surface of the case 3 is contaminated, the surface resistance $R_4$ decreases. When an $SF_6$ gas is pyrolyzed by the arc generated when the breaking unit of the gas insulating device 8 is operated, decomposition products, such as a sulfur fluoride gas, examples of which are $SF_4$ and $S_2F_2$, or finely-divided metal fluoride, are generated. The amount of decomposition products generated increases with the magnitude of the arc current. Among them, when metal fluoride adheres to the case 3 and the case 3 becomes contaminated, the surface resistance $R_4$ decreases. Moreover, it is expected that the degree of the contamination of the case 3 increases in accordance with the cumulative number of breaker operations.

Therefore, in the present embodiment, the surface area of the case 3 is increased by providing the pleated portion 17 on the case 3 in order to obtain a structure with which the case 3 can ensure a large surface resistance even when the case 3 is contaminated. Accordingly, the effect of a leakage current can be suppressed and the combined impedance can be accurately measured.

As described above, in the present embodiment, the case 3 is provided with the pleated portion 17; therefore, even if the surface of the moisture sensor 20 is contaminated by decomposition products of the insulating gas, the effect of a leakage current can be suppressed. Therefore, according to the present embodiment, the AC impedance can be accurately measured and thus the moisture concentration in the insulating gas can be obtained with high accuracy.

Moreover, in the present embodiment, the reduction of the surface resistance $R_4$ is compensated for by correcting the measured value of the AC impedance measured by the impedance measuring circuit 4 in accordance with the cumulative number of breaker operations and the arc current value; therefore, an effect is obtained where the accuracy of the measured value of the moisture concentration further increases. In other words, in the present embodiment, while an error due to the contamination of the surface of the case 3 is structurally suppressed by providing the pleated portion 17 on the case 3, an error is eliminated by correcting the measured value of the AC impedance in accordance with the cumulative number of breaker operations and the arc current value while.

With the moisture concentration detecting device 30, while providing the pleated portion 17 on the case 3, the configuration can be such that a process is omitted of correcting the AC impedance in accordance with the cumulative number of breaker operations and the arc current value (i.e., the breaking information acquiring unit 15, the number-of-breaker-operations storing unit 6a, and the arc-current-value storing unit 6b are omitted). Even in such a case, an error due to the contamination of the surface of the case 3 can be suppressed by providing the pleated portion 17 on the case 3; therefore, the moisture concentration in the insulating gas can be measured with high accuracy.

Moreover, with the moisture concentration detecting device 30, while performing a process of correcting the AC impedance in accordance with the cumulative number of breaker operations and the arc current value, the configuration can be such that the case 3 is not provided with the pleated portion 17. Even in such a case, an error can be eliminated by correcting the measured value of the AC impedance in accordance with the cumulative number of breaker operations and the arc current value; therefore, the moisture concentration in the insulating gas can be measured with high accuracy.

Moreover, in the present embodiment, because the pipe 51 is provided with the blower 9, the insulating gas in the pipes 51 can be blown in by the blower 9 and a gas convection environment can be created around the moisture sensor 20. As described above, by causing the insulating gas to blow in, the measurement time of the moisture concentration can be shortened compared with a case where the moisture concentration is measured in a static gas atmosphere. In other words, creation of a gas convection environment in the gas chamber 31 shortens the time until the moisture concentration of the solid electrolyte membrane 2 comes to equilibrium with the moisture concentration in the insulating gas in the gas insulating device 8; therefore, it is possible to enhance the responsiveness of the impedance element 25 and shorten the measurement time of the moisture concentration.

Second Embodiment

Figure 5:
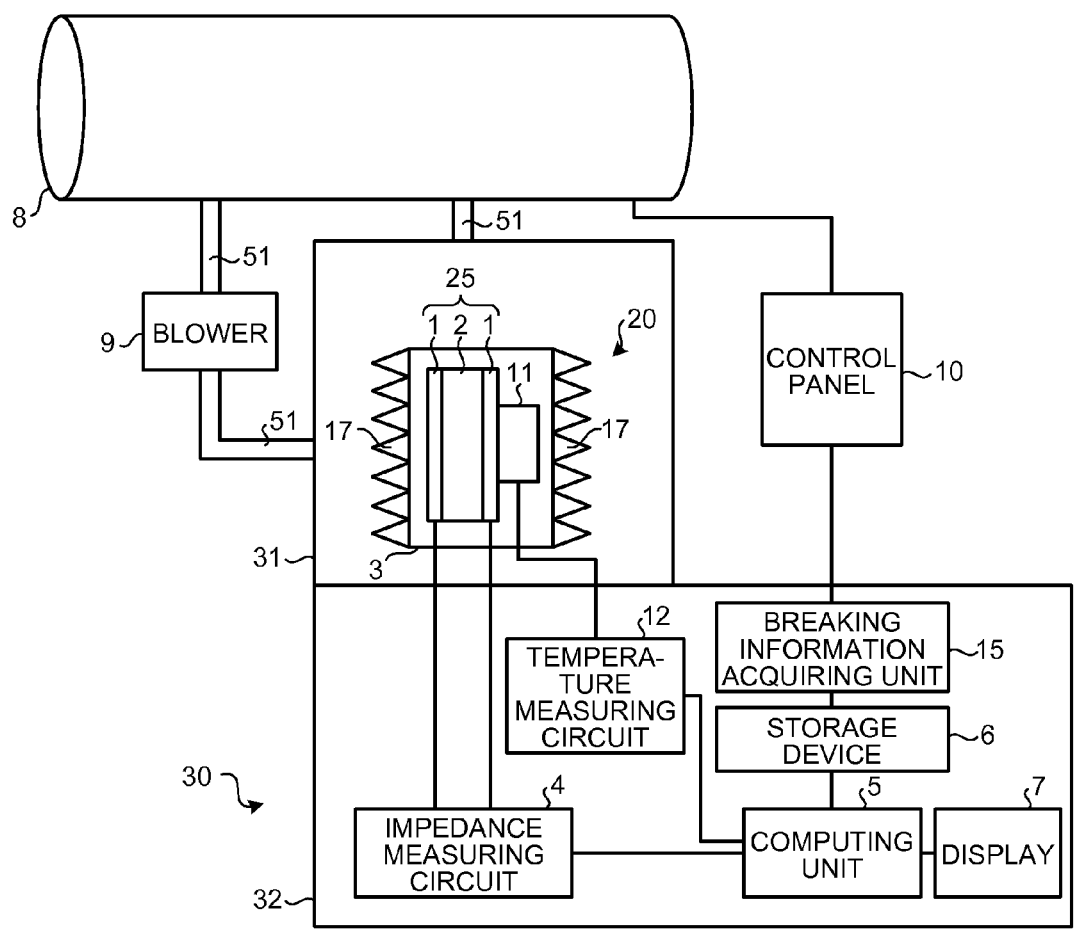
FIG. 5 is a diagram illustrating the configuration of a moisture concentration detecting device according to a second embodiment.

FIG. 5 is a diagram illustrating the configuration of a moisture concentration detecting device according to the present embodiment. As illustrated in FIG. 5, in the present embodiment, the electrode 1 is provided with a temperature sensor 11 and the temperature sensor 11 can measure the temperature of the moisture sensor 20. Moreover, a temperature measuring circuit 12 (temperature measuring unit) connected to the temperature sensor 11 is provided in the signal processing chamber 32. The temperature measuring circuit 12 outputs the temperature that is in accordance with the output from the temperature sensor 11 to the computing unit 5.

The temperature characteristics of the solid electrolyte membrane 2 will be explained here. The AC impedance of the solid electrolyte membrane 2 changes depending on the moisture content and the amount of change thereof has characteristics such that it depends on the temperature of the solid electrolyte membrane 2. Because the temperature characteristics exhibit non-linear characteristics, when the moisture concentration is detected, it is necessary to perform a correcting process on the temperature characteristics. In this correcting process, it is necessary to use a non-linear equation or refer to a special table.

Therefore, in the present embodiment, the temperature of the moisture sensor 20 (i.e., temperature of the solid electrolyte membrane 2) is measured by the temperature sensor 11, and the moisture concentration is detected by the computing unit 5 only when the output of the temperature measuring circuit 12 is within a preset specific temperature range. Specifically, the computing unit 5 obtains the moisture concentration in the insulating gas only when the temperature output from the temperature measuring circuit 12 is within a specific temperature range and does not perform a process of obtaining the moisture concentration in other cases. Accordingly, it is possible to reduce the measurement error of the moisture concentration due to the effect of the temperature characteristics without using a non-linear equation, a special table, or the like.

INDUSTRIAL APPLICABILITY

The present invention is suitable for a moisture concentration detecting device that detects the moisture concentration in an insulating gas with which the gas insulating device is filled.

REFERENCE SIGNS LIST 1 electrode
2 solid electrolyte membrane
3 case
4 impedance measuring circuit
5 computing unit
6 storage device
6a number-of-breaker-operations storing unit
6b arc-current-value storing unit
6c impedance-correction-information storing unit
6d conversion information storing unit
7 display
8 gas insulating device
9 blower
10 control panel
11 temperature sensor
12 temperature measuring circuit
15 breaking information acquiring unit
17 pleated portion
20 moisture sensor 25 impedance element
30 moisture concentration detecting device
31 gas chamber
32 signal processing chamber
51 pipe

The invention claimed is:

1. A moisture concentration detecting device that detects a moisture concentration in an insulating gas with which a gas insulating device is filled, the device comprising:
   a gas chamber into which the insulating gas is introduced from an inside of the gas insulating device;
   a pair of porous electrodes that are arranged to face each other in the gas chamber;
   a solid electrolyte membrane fixed such that the solid electrolyte membrane is sandwiched between the electrodes;
   a case which covers the pair of electrodes and the solid electrolyte membrane and on a surface of which a pleated portion is provided;
   an impedance measuring unit that measures an AC impedance between the electrodes by applying an AC voltage to the pair of electrodes;
   a storage device that stores therein conversion information for converting an AC impedance between the electrodes into a moisture concentration in the insulating gas; and
   a moisture concentration detecting unit that obtains a moisture concentration in the insulating gas from a measured value of the AC impedance by referring to the conversion information stored in the storage device with respect to the measured value of the AC impedance input from the impedance measuring unit.

2. The moisture concentration detecting device according to claim 1, wherein
   the gas insulating device is a gas insulated circuit breaker,
   the storage device stores therein, in addition to the conversion information, arc-current-value information on a current value of an arc generated when the gas insulated circuit breaker operates, cumulative-number-of-breaker-operations information on cumulative number of operations of the gas insulated circuit breaker, and impedance correction information for correcting a measured value of an AC impedance between the electrodes in accordance with the arc-current-value information and the cumulative-number-of-breaker-operations information, and
   when a measured value of the AC impedance is input from the impedance measuring unit, the moisture concentration detecting unit obtains the arc-current-value information and the cumulative-number-of-breaker-operations information by referring to the storage device, obtains impedance correction information in accordance with the arc-current-value information and the cumulative-number-of-breaker-operations information from the storage device, thereafter, corrects the measured value of the AC impedance by using the impedance correction information, and obtains a moisture concentration in the insulating gas from a corrected measured value of the AC impedance by referring to the conversion information stored in the storage device with respect to the corrected measured value of the AC impedance.

3. The moisture concentration detecting device according to claim 1, wherein
   the gas insulating device and the gas chamber are connected to each other with two pipes, and
   at least one of the pipes is provided with a blower that blows in the insulating gas in the pipes.

4. The moisture concentration detecting device according to claim 1, further comprising a temperature sensor capable of measuring a temperature of the solid electrolyte membrane, wherein
   the moisture concentration detecting unit obtains a moisture concentration in the insulating gas only when a temperature detected by the temperature sensor is within a specific temperature range.

* * * * *